United States Patent
Madden

[11] 3,941,485
[45] Mar. 2, 1976

[54] DEVICE FOR CONTINUOUSLY MEASURING A DIMENSION OF A WORKPIECE BY REFLECTED LIGHT

[76] Inventor: Richard A. Madden, Meetinghouse Lane, Little Compton, R.I. 02837

[22] Filed: Nov. 8, 1973

[21] Appl. No.: 413,962

[52] U.S. Cl............. 356/159; 350/96 B; 350/96 C; 356/199
[51] Int. Cl.²................. G01B 11/04; G01B 11/10
[58] Field of Search .......... 356/159, 199, 200, 209; 250/560, 571, 227; 350/96 B

[56] References Cited
UNITED STATES PATENTS

| | | | |
|---|---|---|---|
| 2,471,800 | 5/1949 | Von Mulinen | 350/96 B |
| 2,810,316 | 10/1957 | Snyder | 356/159 |
| 3,466,928 | 9/1969 | Kind | 350/96 B |
| 3,566,083 | 2/1971 | McMillin | 250/227 |
| 3,655,989 | 4/1972 | Robinson | 356/159 |

Primary Examiner—Vincent P. McGraw
Attorney, Agent, or Firm—Maurice R. Boiteau

[57] ABSTRACT

There is disclosed in the present application apparatus for continuously measuring a dimension such as the gage of a strand on the thickness of a web by a plurality of reflections of light focused on points at varying distances from the normal center line of the path of the strand or web. The light is conveyed to the various points of a set from a common light source through fibrous light guides and if reflected by the strand or web at a specific point, the light is conveyed to a display board through a light guide of a second set to indicate the size of the strand or web.

7 Claims, 6 Drawing Figures

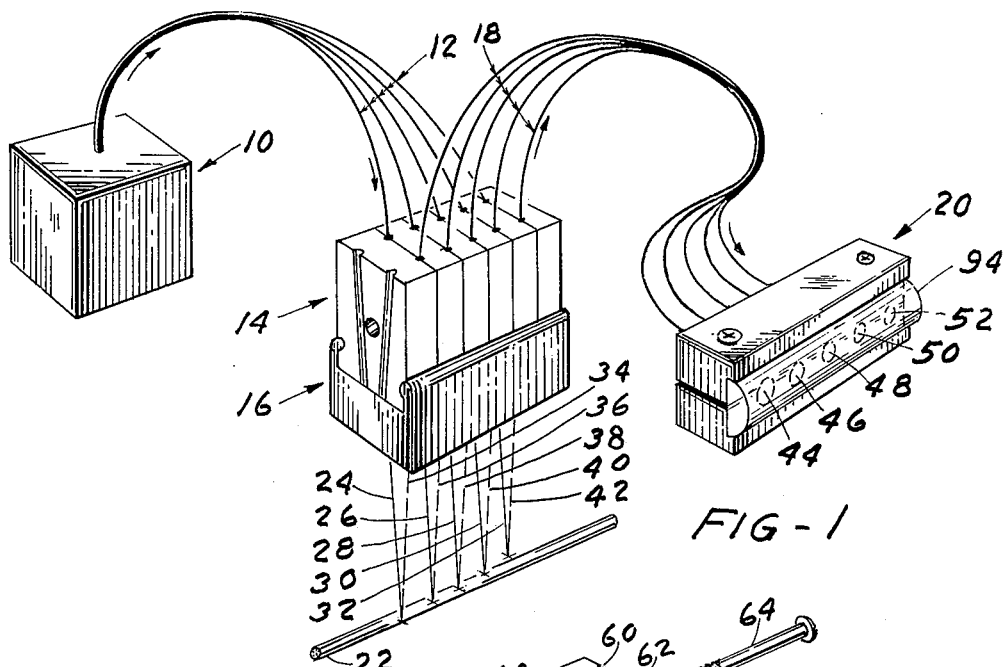
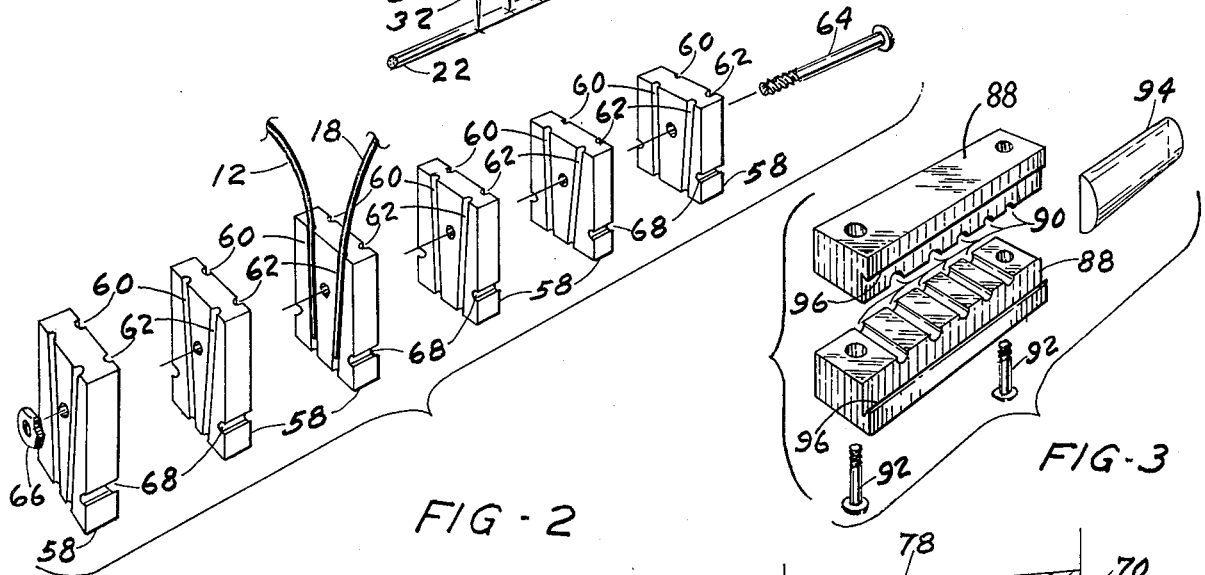
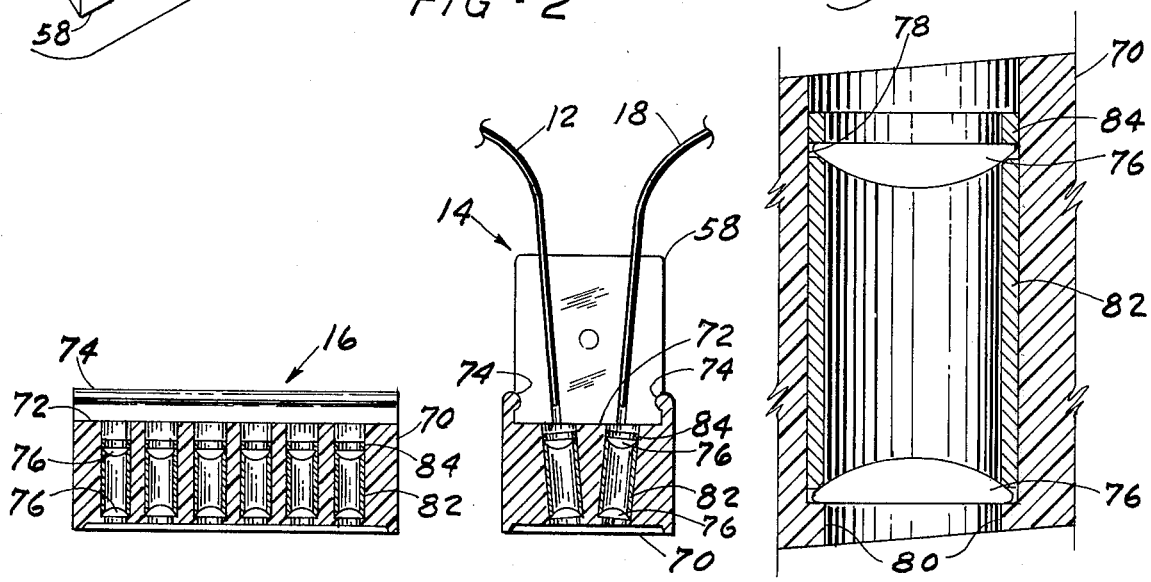

DEVICE FOR CONTINUOUSLY MEASURING A DIMENSION OF A WORKPIECE BY REFLECTED LIGHT

The present invention relates generally to improvements in apparatus for continuously measuring a dimension such as the gage of a strand or the thickness of a web and generally but not necessarily while the strand or web is in motion. Dimensions which may be measured by the apparatus include the gage of strands ranging from metallic wire and rod, extruded rods of various plastics, monofilament and multifilament yarns, non twisted tows in early textile processing, and cords and ropes of either synthetic or natural fibers. Among the webs whose thickness may be measured by the apparatus according to the invention are paper, cloth and films of various synthetic materials and coatings applied to such webs. In addition, the present apparatus is also applicable to liquid and incompletely solidified streams. More particularly, the present invention is directed to continuous measuring apparatus in which measurements are obtained by the reflection of light without imposing any stress upon the strand or web which may be fragile and easily distorted or otherwise changed by the stress.

In various manufacturing processes including wire drawing, papermaking, film blowing and extrusion, spinning of natural and synthetic fibers and the like, a constant check on the diameter or thickness of the product is highly desirable in order to avoid a defective product, either one having a very temporary defect or one in which a change in machine adjustment introduces a dimension which drifts gradually outside its normally acceptable range. Such a check which may be continuously observed is sometimes very difficult to obtain in a usable and reliable form. One of the problems is that many such measuring devices include parts which are subject to wear and to a consequent loss of accuracy which renders them unreliable for the intended purpose. Another problem which is frequently encountered is that some of the measuring devices require physical contact with the product and that as a result the product is either marked or in some other way damaged in an unacceptable manner.

It is accordingly an object of the present invention to improve the durability and reliability of measuring devices applicable to the continuous checking of dimensions.

Another object is to provide for the continuous measurement of product dimensions without subjecting the product to objectionable distortion or marking.

Yet another object is the checking of dimensions on a product while the product remains in motion.

Still another object is the measurement of dimensions in a plurality of steps while establishing readily observable indicia of maximum and minimum limits of the measured dimension in the product.

The foregoing objects are achieved in accordance with the present invention by a measuring device in which measurement is accomplished by means of light beams focused upon and reflected from points on and adjacent to the product. According to a feature of the invention, light is transmitted from a common light source through a first set of light guides and focused by projection lenses upon points on and adjacent the product. A second set of light guides is associated with a second set of lenses to conduct light which impinges upon the product back to a display panel which indicates continuously the dimension being measured. When a particular beam fails to impinge upon the product, the light is not reflected and accordingly does not appear at the display panel thereby indicating that the product dimension is smaller than necessary to reflect the light from a given projection lens to a related position on the display panel.

The foregoing objects, features and numerous advantages of the present invention will be more fully understood from a detailed description of an illustrative embodiment taken in connection with the accompanying drawings in which:

FIG. 1 is a view in perspective and shown partly schematically of a measuring apparatus according to the present invention, including a multiple lens carrier forming part of a lens assembly and a display panel;

FIG. 2 is an exploded view in perspective of clamps for holding light guides at the lens assembly of FIG. 1;

FIG. 3 is an exploded view of the display panel of FIG. 1;

FIG. 4 is a view in longitudinal section taken through one set of lenses either projection or reflection at the lens carrier;

FIG. 5 is a transverse section showing a related pair of projection and reflection lenses and associated light guides; and FIG. 6 is a view in cross-section showing the details of one of the lenses depicted in FIG. 5.

Turning now to the drawings, there is depicted an apparatus including a light box indicated generally at 10 and enclosing a common light source in the form of an appropriate lamp (not shown). For many applications, an ordinary incandescent lamp may be used. For difficult environments in which there is a high level of illumination, however, the light source may be a projection lamp or a high intensity lamp such as that sold by American Optical Company of Southbridge, Mass. as Catalog No. EJY for its 11-80 Illuminator. A plurality of projection light guides 12 is shown schematically directing light to clamp and lens assemblies indicated generally at 14 and 16 respectively. Reflection light guides shown schematically at 18 direct light to a display panel indicated generally at 20. The light guides 12 and 18 may be of any conventional form either multifilament employing glass or plastic fibers or the less expensive monofilament guides. The choice depends on the tolerance, the product and the environment.

In the drawings, there is shown an apparatus for directing light from a common source to five distinct points at or near a product which may be thought of as a strand 22. From left to right are schematically shown projection beams 24, 26, 28, 30 and 32 and reflection beams 34, 36, 38, 40 and 42. As depicted in FIG. 1, the projection beam 28 is aimed at the center line of the strand 22 and accordingly whenever a workpiece of any size is present will show reflected light at a first indicator 44 on the display panel 20. It is seen from FIG. 1 that beams 26, 30, 24 and 32 are aimed at points progressively farther away from the center line of the strand 22. Accordingly, as the projection beam 26 is reflected, light appears at a second indicator spot 46 showing an increment in the thickness of the strand 22 as measured by the apparatus. Similarly, the projection beam 30 when reflected from the strand 22 produces light at a third indicator spot 48 thereby indicating a second increment of the observed dimension. Finally, the reflections of the beams 24 and 32 show light at indicator spots 50 and 52 respectively to indicate third and fourth size increments of the strand 22. In practice, the projection beams 24, 26, 28, 30 and 32 are aimed to divide the tolerance band applicable to the product so that when the dimension is running at approximately the mid-range of its band, three beams are reflected and accordingly there is light showing at 44, 46 and 48. When the light then appears at 50, this is taken as a signal to the operator that the dimension is increasing and will exceed its tolerance when light appears at 52 as a result of the projection light beam 32 being reflected from the strand 22. Similarly, when the light no longer appears at the location 48, this is a signal to the operator that the dimension of the strand 22 is decreasing toward the lower limit of the tolerance band which will be reached when the light at 46 disappears.

It is obvious that the above-described arrangement in which the dimension is measured in four increments may be altered to suit circumstances such as the degree of precision required by the nature of the product. If more precision is required, it may be obtained by a larger number of beams dividing the tolerance band into a greater number of increments and similarly a smaller number of beams may be used if the measurement requires less precision obtained in fewer increments.

In the measurement of the width of a tape for example, essentially the same type of arrangement as above-described is employed. However, for measuring a dimension such as a thickness of a web, it is preferable to focus the beams in a line at a roll over which the web is trained. Each successive beam is aimed at a greater distance from the roll over which the web passes. Thus, the nearest projection beam is focused generally tangent to the roll and is accordingly not reflected if no web is passing over the roll. Successive beams are at greater distances and by showing light at successive positions on the display panel indicate added increments in the thickness of the web in accordance with a predetermined arrangement.

A typical light guide 12 is fitted with a metal end tip which may conveniently be gripped at the light box 10, at the clamp assembly 14, and at the display panel 20. At the light box 10, a plurality of appropriately directed perforations in the box may be employed for receiving individual metal end tips of individual light guides 12 aimed at the lamp and appropriately clamped. The other end of the projection guides 12 is secured by the clamp assembly 14 in alignment each with its related lens. The clamp assembly 14 comprises a plurality of like blocks 58 formed on each side with a pair of grooves for orienting projection and reflection light guides. Thus grooves 60 in adjacent blocks are used to align a projection light guide while grooves 62 of adjacent blocks are employed for directing a reflection light guide. As is seen from FIG. 2, the set of blocks 58 consisting of six blocks is clamped together by means of a screw 64 and a nut 66 to secure two sets of light guides, five projection guides 12, and five reflection guides 18. Each of the blocks 58 is additionally notched at 58 to receive a lens carrier 70 forming a part of the lens assembly 16.

The lens carrier 70 is in the form of a block, the upper surface of which is shaped with a slot 72 and a pair of opposed inwardly directed integral strips 74 adapted to fit the notches 68 of the blocks 58 fixedly to suspend the lens assembly 16 from the clamp assembly 14. For each beam whether a projection beam or a reflection beam, there is provided in the carrier 70 a lens couple comprising a pair of planar-convex lenses 76 forming a condenser to gather and concentrate light first from the projection guides 12 to direct the light in a beam converging narrowly at the product to be measured and then to gather the light reflected from the product and direct it toward the reflection guide 18. As best seen in FIG. 6, each condenser lens arrangement is inserted in a counterbore 78 of an opening 80, the bottom of the counterbore providing a nest for the lowermost of the lenses 76. The two lenses 76 of the condenser couple are separated by a tubular spacer 82 and are secured in position by a ring 84 which is frictionally retained in the counterbore. It is altogether possible that in some applications different optical arrangements would be employed. For instance, the lens couples which have already been described as alike may be different in some applications to suit the circumstances of product cross-section and reflectivity, the environmental illumination and the tolerance to be measured. However, regardless of the lenses employed, it will be appreciated that there is provided according to the invention a plurality of projection light paths and a plurality of reflection light paths leading to a location where an observer may determine the magnitude of a workpiece dimension from the number of beams reflected to the location.

For convenience in the presentation of the indicators, the display panel includes a pair of clamp bars 88 each formed with a plurality of spaced-apart locating notches 90. The bars are appropriately drilled and secured together by screws 92 so as to hold the metal end tips of the reflection light guides between notches of the two bars 88. In order to improve the visibility of the indicator reflections 44, 46, 48, 50 and 52, an elongated convex magnifier 94 is provided at the front face of the clamp bars 88 to enlarge the image of the ends of the light guides. The magnifier 94 is retained by undercut lips 96 on the forward face of the bars 88.

Having thus disclosed my invention, what I claim as new and desire to secure by Letters Patent of the United States is:

1. Apparatus for continuously measuring a narrow work-piece in motion along a pre-determined linear path comprising a common light source, means for projecting a plurality of light beams toward points spaced longitudinally along and at varying distances laterally from the center of the path, visual display means for exhibiting a plurality of discrete light beams reflected from the work-piece, means for conducting light from the light source to the means for projecting each light beam and means for directing reflected light from the work-piece to the visual display means whereby the width of the work-piece is determined in steps by the number of light beams appearing at the visual display means.

2. Apparatus according to claim 1 further characterized in that the light conducting means comprises a set of light guides one between the light source and each projecting means.

3. Apparatus according to claim 2 further characterized in that the reflected light directing means comprises a second set of light guides interposed between the work-piece and the visual display means.

4. Apparatus according to claim 1 further characterized in that each light projecting means and each light directing means includes at least one lens.

5. Apparatus according to claim 1 further comprising lens means for gathering reflected light and focussing it upon the light directing means.

6. Apparatus according to claim 3 further characterized in that the visual display means comprises means for clamping in separated relationship the ends of the light guides remote from the work-piece.

7. Apparatus according to claim 6 further characterized in that the visual display means includes a lens magnifying the ends of the light guides.

* * * * *